United States Patent [19]

Anderson et al.

[11] Patent Number: 5,354,767
[45] Date of Patent: Oct. 11, 1994

[54] RENIN INHIBITING POLYHYDROXY-MONOAMIDES

[75] Inventors: Paul C. Anderson, Pierrefonds; Gary W. Bantle, St. Laurent; Grace L. Jung, Montreal; Pierre Lavallée, Rosemère; Bruno Simoneau, Laval, all of Canada

[73] Assignee: Bio-Mega, Inc., Laval, Canada

[21] Appl. No.: 990,779

[22] Filed: Dec. 10, 1992

[30] Foreign Application Priority Data

Dec. 30, 1991 [CA] Canada ................... 2058603

[51] Int. Cl.$^5$ ............ C07C 235/34; A61K 31/16
[52] U.S. Cl. .................. 514/365; 514/370; 514/400; 514/438; 514/622; 548/194; 548/204; 548/338.1; 549/77; 564/174
[58] Field of Search ........... 564/174; 548/194, 204, 548/342; 549/77; 514/365, 370, 400, 438, 622

[56] References Cited

U.S. PATENT DOCUMENTS 5,032,577 7/1991 Fung .................. 514/18

OTHER PUBLICATIONS

Kempf, J. Med. Chem. 33 371(1990).

*Primary Examiner*—Robert Gerstl
*Attorney, Agent, or Firm*—D. E. Frankhouser; A. R. Stempel; M-E. M. Timbers

[57] ABSTRACT

Disclosed herein are compounds of the formula:

$$R^1CH_2CH(X)CH(Y)CH(Z)CHR^2C(O)NHCHR^3CH(OH)CH(OH)R^4$$

wherein $R^1$ is a terminal unit, for example lower cycloalkyl or phenyl; $R^2$ is, for example, an optionally substituted alkyl, cycloalkylmethyl, benzyl, 4-imidazolylmethyl, 2-thienylmethyl or 4-thiazolylmethyl; $R^3$ is alkyl, cycloalkylmethyl or an optionally substituted benzyl; $R^4$ is alkyl or cycloalkyl; and X and Y each is hydroxy and Z is hydrogen, or X and Z each is hydroxy and Y is hydrogen; with the provisos that (a) the carbon atom bearing $R^2$ has the "R" configuration except when $R^2$ is 2-thienylmethyl or 2-thiazolylmethyl, X and Y each is hydroxy and Z is hydrogen, then the carbon atom bearing $R^2$ has the "S" configuration; (b) the carbon atoms bearing $R^3$ and $R^4$ each has the "S" configuration; and (c) the carbon atom located between the last-said two carbon atoms has the "R" configuration. The compounds inhibit renin activity and are indicated for the treatment of hypertension and congestive heart failure.

7 Claims, No Drawings

RENIN INHIBITING POLYHYDROXY-MONOAMIDES

FIELD OF INVENTION

This invention relates to compounds exhibiting renin inhibiting properties, to processes for producing the compounds, to pharmaceutical compositions thereof, to processes and intermediates for preparing the compounds and to methods of treating renin-dependent hypertension and congestive heart failure.

BACKGROUND OF THE INVENTION

The physiological role of the renin-angiotensin system is to regulate blood pressure and to maintain sodium and volume homeostasis. The key events in this system are the conversion of the polypeptide angiotensinogen to the decapeptide angiotensin I (AI) and the subsequent cleavage of the latter to give the octapeptide angiotensin II (AII). The latter peptide is a potent vasoconstrictor and a potentiator of aldosterone release. Due to potent pressor effects, AII plays a significant role in hypertension and as such has been the target for the development of antihypertensive agents.

One approach to finding such agents is to search for potent inhibitors of the angiotensin converting enzyme. Inter alia, the latter enzyme catalyzes the conversion of AI to AII. This approach has met with success and a number of such agents are used therapeutically to treat hypertension. Another approach is to find specific inhibitors of renin, an aspartyl protease which cleaves angiotensinogen to AI. Since angiotensinogen is the only known substrate for renin, this approach has the desirable feature of being aimed at a potential antihypertensive agent with a single mode of action.

The ability of renin inhibitors to lower blood pressure and to reduce plasma renin activity has been demonstrated in the clinic. For a recent review on renin inhibitors, see W. J. Greenlee, Medical Research Reviews, 10, 173 (1990). Nevertheless, progress toward obtaining the ideal renin inhibitor continues to be plagued with problems of low oral absorption, limited bioavailability and rapid elimination, mainly due to the peptidic nature of the inhibitors presently under investigation. Hence, there is a need for a readily administered, effective renin inhibitor.

The renin inhibitors of the present application can be distinguished by their non-peptidic character. The compounds are characterized by being polyhydroxylic, by having only one amide bond and a relatively low molecular weight. These features contribute to the relative stability and absorption of the inhibitors.

The following references exemplify past efforts that have been made in the search for renin inhibitors with improved characteristics:

J. R. Luly et al., U.S. Pat. No. 4,845,079, issued Jul. 4, 1989,

A. K. L. Fung et al., PCT patent application WO 88/05050, published Jul. 14, 1988, H. H. Stein et al., European patent application 311012, published Apr. 12, 1989, A. K. L. Fung et al., European patent application 364804, published Apr. 25, 1990, G. J. Hanson et al., Biocheb. Biophys. Res. Commun., 146, 959 (1987), G. J. Hanson et al., Biocheb. Biophys. Res. Commun., 160, 1 (1989), D. J. Kebpf et al., J. Med. Chem., 33, 371 (1990), and D. J. Kebpf and S. L. Condon, J. Org. Chem., 55, 1390 (1990).

SUMMARY OF THE INVENTION

The compounds of the present application are represented by formula 1

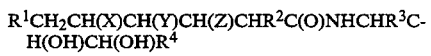

$$R^1CH_2CH(X)CH(Y)CH(Z)CHR^2C(O)NHCHR^3CH(OH)CH(OH)R^4 \qquad 1$$

wherein $R^1$ is lower alkyl; lower alkyl monosubstituted with hydroxy, lower alkoxy or benzyloxy; lower cycloalkyl; phenyl; phenyl monosubstituted with hydroxy, lower alkyl, lower alkoxy or halo; 1-naphthyl; or 2-naphthyl;

$R^2$ is lower alkyl; lower alkyl monosubstituted with hydroxy, lower alkoxy or benzyloxy; (lower cycloalkyl)methyl; benzyl; 4-imidazolylmethyl; 2-thienylmethyl; 2-thiazolylmethyl; 4-thiazolylmethyl; 2-methyl-4-thiazolylmethyl; or 2-amino-4-thiazolylmethyl;

$R^3$ is lower alkyl; (lower cycloalkyl)methyl; benzyl; or benzyl monosubstituted on the aromatic portion thereof with hydroxy, lower alkyl or lower alkoxy;

$R^4$ is lower alkyl or lower cycloalkyl;

X and Y each is hydroxy and Z is hydrogen, or X and Z each is hydroxy and Y is hydrogen; with the provisos that (a) the carbon atom bearing $R^2$ has the (R) configuration, except when $R^2$ is 2-thienylmethyl or 2-thiazolylmethyl, X and Y each is hydroxy and Z is hydrogen, then the carbon atom bearing $R^2$ has the (S) configuration; (b) the carbon atoms bearing $R^3$ and $R^4$ each has the (S) configuration; and (c) the carbon atom located between the latter two carbon atoms has the (R) configuration.

A preferred group of the compounds of the present application is represented by formula 1 wherein $R^1$ is phenyl, 4-hydroxyphenyl, 4-methoxyphenyl, 2-fluorophenyl or 1-naphthyl; $R^2$ is cyclopropylmethyl, cyclopentylmethyl, cyclohexylmethyl, benzyl, 4-imidazolylmethyl, 2-thienylmethyl, 4-thiazolylmethyl or 2-amino-4-thiazolylmethyl; $R^3$ is 2-methylpropyl, cyclopropylmethyl, cyclohexylmethyl or benzyl; and $R^4$ is lower alkyl or lower cycloalkyl.

A more preferred group of the compounds represented by formula 1 wherein $R^1$ is phenyl, 4-methoxyphenyl or 1-naphthyl; $R^2$ is cyclopropylmethyl, 4-imidazolylmethyl, 2-thienylmethyl, 4-thiazolylmethyl, 2-methyl-4-thiazolylmethyl or 2-amino-4-thiazolylmethyl; $R^3$ is as defined in the last instance; and $R^4$ is lower alkyl or lower cycloalkyl.

A most preferred group of this compound is represented by formula 1 wherein $R^1$ is phenyl; $R^2$ is cyclopropylmethyl, 4-thiazolylmethyl or 2-amino-4-thiazolylmethyl; $R^3$ is cyclohexylmethyl; and $R^4$ is 2-methylpropyl or cyclopropyl.

Included within the scope of this invention is a pharmaceutical composition for treating renin-dependent hypertension comprising a compound of formula 1 and a pharmaceutically acceptable carrier.

Also included in this invention is a method of treating renin-dependent hypertension or congestive heart failure in a mammal comprising administering thereto a blood pressure-lowering effective amount of the compound of formula 1.

Processes for preparing the compounds of formula 1 are described hereinafter.

DETAILS OF THE INVENTION

General

The compounds of formula 1 can alternatively be illustrated as:

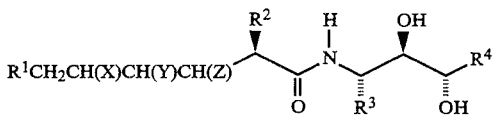

The compounds of formula 1 are monoamide derivatives having an acyl portion and an amino portion. Each portion contains three chiral centers residing in the principal linear axis (i.e. the backbone) of the compounds. The chirality of the amino portion is fixed whereby the central carbon atom of the three adjoining asymmetric carbon atoms has a (R) configuration and the two flanking asymmetric carbon atoms have the (S) configuration. The chirality of the acyl portion allows that radical to exist in various optically active or racemic forms. All such forms are included for the compounds of formula 1 and for their appropriate intermediates therefore. For the asymmetric carbon atom adjacent to the amide group, i.e. the carbon atom bearing $R^2$, the preferred configuration is (R) except when $R^2$ is 2thienylmethyl or 2-thiazolylmethyl, X and Y each is hydroxy and Z is hydrogen, then the preferred configuration of the carbon atom bearing $R^2$ is (S). With respect to the remaining two asymmetric centers of the acyl radical, i.e. the carbon atoms bearing a hydroxyl, the two respective hydroxyls of these carbon atoms can exist in the four possible combinations of (R) and (S) configurations, i.e. (RR), (RS), (SR) and (SS). Consequently, the compounds of this invention can be diastereoisomeric mixtures, with the respect to these two centers, or they can be individual diastereoisomers.

The term "lower alkyl" as used herein, either alone or in combination with a radical, means straight chain alkyl radicals containing one to four carbon atoms and branched chain alkyl radicals containing three to four carbon atoms and includes methyl, ethyl, propyl, butyl, 1-methylethyl, 1methylpropyl, 2-methylpropyl and 1,1-dimethylethyl.

The term "lower cycloalkyl" as used herein, either alone or in combination with a radical, means saturated cyclic hydrocarbon radicals containing from three to six carbon atoms and includes cyclopropyl, cyclobutyl, cyclopentyl and cyclohexyl.

The term "lower alkoxy" as used herein means straight chain alkoxy radicals containing one to four carbon atoms and branched chain alkoxy radicals containing three to four carbon atoms and includes methoxy, ethoxy, propoxy, 1-methylethoxy, butoxy and 1,1-dimethylethoxy. The latter radical is known commonly as tertiary-butyloxy.

The term "halo" as used herein means a halo radical selected from bromo, chloro, fluoro or iodo.

The term "coupling agent" as used herein means an agent capable of effecting the dehydrative coupling of a carboxy group of one compound with a free amino group of another compound to form an amide bond between the reactants. The agents promote or facilitate the dehydrative coupling by activating the carboxy group. Descriptions of such coupling agents and activated groups are included in general textbooks of peptide chemistry; for instance, E. Schröder and K. L. Lubke, "The Peptides", Vol. 1, Academic Press, New York, N.Y., 1965, pp 2–128, and K. D. Kopple, "Peptides and Amino acids", W. A. Benjamin, Inc., New York, N.Y., 1966, pp 33–51. Examples of coupling agents are thionyl chloride, diphenylphosphoryl azide, dicyclohexylcarbodiimide, N-hydroxysuccinimide, or 1-hydroxybenzotriazole in the presence of dicyclohexylcarbodiimide. A very practical and useful coupling agent is (benzotriazol-1-yloxy)tris(dimethylamino)phosphonium hexafluorophosphate, described by B. Castro et al., Tetrahedron Letters, 1219 (1975), see also D. Hudson, J. Org. Chem., 53, 617 (1988), either by itself or in the presence of 1-hydroxybenzotriazole.

The term "pharmaceutically acceptable carrier" as used herein means a non-toxic, generally inert vehicle for the active ingredient, which does not adversely affect the ingredient.

The term "effective amount" as used herein means a predetermined amount of the compound of formula 1 sufficient to lower blood pressure on being administered to a mammal.

Process

Note that with respect to the compounds of formulae 2, 3 and 4 appearing hereafter, the aforementioned provisos regarding the stereochemisty of $R^2$, $R^3$, $R^4$ and the carbon atom located between $R^3$ and $R^4$ of formula 1 apply as well to the corresponding carbon atoms of these compounds.

The compounds of formula 1 can be prepared by a process in which the key step involves the coupling, by means of a coupling agent, of a protected polyhydroxy carboxylic acid of formula 2

$$R^1CH_2CH(X^1)CH(Y^1)CH(Z^1)CHR^2COOH \qquad 2$$

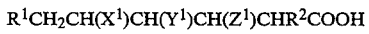

wherein $R^1$ and $R^2$ are as defined herein; and $X^1$ is $OW^a$ wherein $W^a$ is a hydroxy protecting group, $Y^1$ is $OW^b$ wherein $W^b$ is a hydroxy protecting group and $Z^1$ is hydrogen, or $X^1$ is $OW^a$ wherein $W^a$ is a hydroxy protecting group, $Y^1$ is hydrogen and $Z^1$ is $OW^b$ wherein $W^b$ is a hydroxy protecting group; with an aminodiol of formula 3

$$NH_2CHR^3CH(OH)CH(OH)R^4 \qquad 3$$

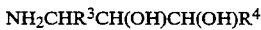

wherein $R^3$ and $R^4$ are as defined herein to obtain the corresponding protected monoamide of formula 4

$$R^1CH_2CH(X^1)CH(Y^1)CH(Z^1)CHR^2\text{-}C(O)NHCHR^3CH(OH)CH(OH)R^4 \qquad 4$$

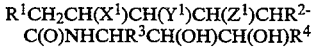

wherein $R^1$, $R^2$, $R^3$, $R^4$, $X^1$, $Y^1$ and $Z^1$ are as defined herein, followed by deprotection of the monoamide of formula 4 by the use of appropriate deprotecting agents to give the corresponding compound of formula 1.

With more specific reference to the term "hydroxy protecting group" as used with reference to $W^a$ and $W^b$ of the compounds of formula 2 and 4, the term encompasses both a first situation wherein $W^a$ and $W^b$ each is a hydroxy protecting group and a second situation wherein $W^a$ and $W^b$ are joined, forming an acetal type protecting group which protects them asked hydroxyls of the compounds. In the first situation, which can be applied generally to processes described herein, examples of a hydroxy protecting group include benzyl, 4-methoxybenzyl and tert-butyldimethylsilyl. In the second situation which is applied herein with respect to the polyhydroxy carboxylic acids of formula 2 in which $X^1$ is $OW^a$, $Y^1$ is hydrogen and $Z^1$ is $OW^b$, $W^a$ and $W^b$ jointly represent a divalent radical of formula $CR^aR^b$ wherein $R^a$ and $R^b$ each is lower alkyl (preferably methyl or ethyl) so that $W^a$ and $W^b$, together with the oxygen atoms to which they are attached and in turn the three incorporated carbon atoms of the principle linear axis of the compound, form a 2,2-dialkyl-[1,3]dioxane ring system.

The requisite protected polyhydroxy carboxylic acid of formula 2 can be prepared by processes designed to give the desired stereochemistry and position of the hydroxy groups. Practical processes for this purpose are:

Firstly, the requisite carboxylic acid of formula 2 in which $R^1$ and $R^2$ are as defined herein, $X^1$ is $OW^a$, $Y^1$ is $OW^b$ and $Z^1$ is hydrogen ($W^a$ and $W^b$ being hydroxy protecting groups) and each of the carbon atoms bearing $X^1$ and $Y^1$ has the (S) configuration can be prepared by the process illustrated Scheme 1. In Scheme 1, $R^1$ and $R^2$ are as defined herein and $W^a$ is an O-protecting group for a secondary hydroxyl [for example, benzyl, (4-methoxyphenyl)methyl or tert-butyldimethylsilyl].

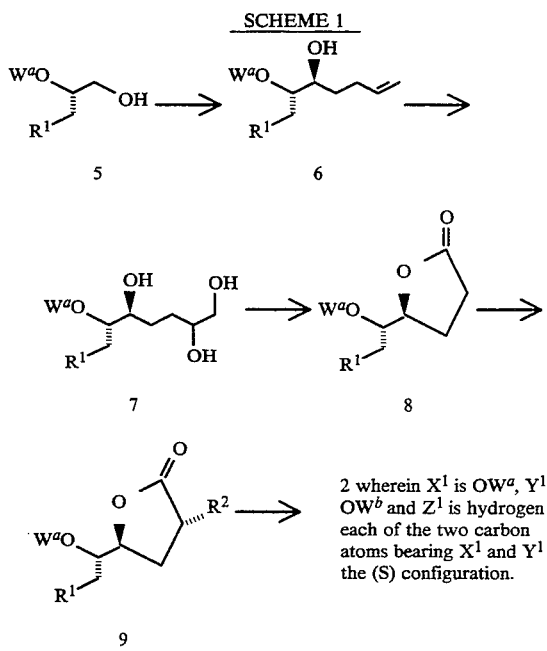

More particularly, according to Scheme 1, the (S)-enantiomer of the monoprotected diol 5 is oxidized with a reagent capable of transforming a primary alcohol to an aldehyde. The resultant aldehyde is allowed to react with 3-butenyl magnesium bromide to give the olefin 6 which upon further oxidation with osmiumtetroxide affords the polyol 7. Subsequent oxidation of the latter compound with sodium periodate, followed by another oxidation of the intermediary hydroxyaldehyde-hemiacetal with Jones' reagent [A. Bowers et al., J. Chem. Soc., 2555 (1953)] provides the lactone 8.

Subsequent alkylation of the lactone with an appropriate alkylation reagent (for example, 2-thienylmethylchloride when the desired carboxylic acid of formula 2 is one in which $R^2$ is 2-thienylmethyl) affords the alkylated lactone of formula 9. (A preferred alternate route to the alkylated lactone of formula 9 in which $R^2$ is cyclopropylmethyl involves alkylation with allyl bromide followed by treatment of the α-allyl lactone with diazomethane in the presence of palladium acetate.) Thereafter, the ring of the lactone 9 is opened under basic conditions and the free hydroxyl of the ring opening product is protected whereby the desired carboxylic acid of formula 2 in which $X^1$ is $OW^a$, Y is $OW^b$ and Z is hydrogen, each of the carbon atoms bearing $OW^a$ and $OW^b$ has the (S) configuration, and $R^1$ and $R^2$ are as defined herein is obtained.

Secondly, the corresponding diol carboxylic acid of formula 2 (of the latter compound) in which $X^1$ is $OW^a$, $Y^1$ is $OW^b$ and $Z^1$ is hydrogen and the carbon atoms bearing the $X^1$ and $Y^1$ have the (R) and (S) configurations, respectively, or the (S) and (R) configurations, respectively, and $R^1$ and $R^2$ are as defined herein can be obtained by a process shown in Scheme 2. In Scheme 2, $R^1$ and $R^2$ are as defined herein, and $W^a$ and $W^b$ each is an O-protecting group for a secondary hydroxyl [for example, benzyl, (4-methoxyphenyl)methyl or tert-butyldimethylsilyl].

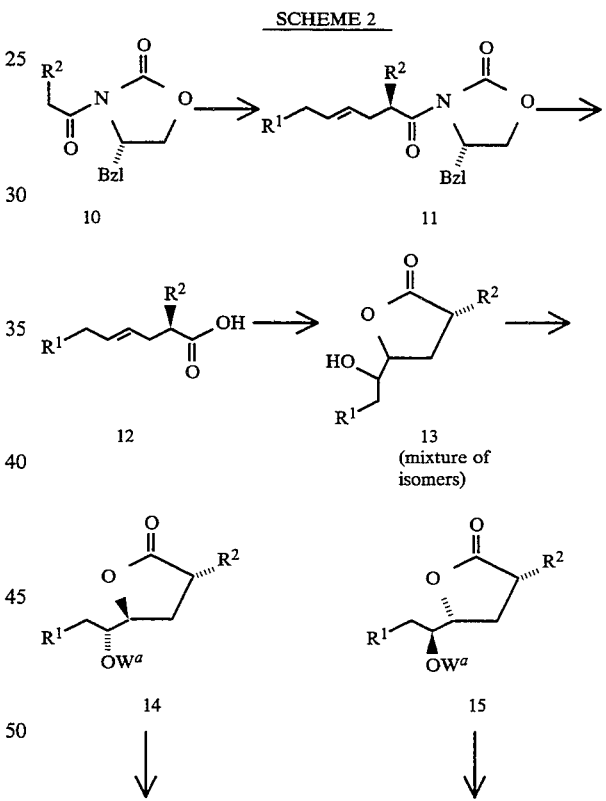

More explicitly, by applying the stereoselective alkylation method of D. A. Evans et al., J. Amer. Chem. Soc., 104, 1737 (1982), the chiral imide 10 is alkylated with the allylic bromide of formula $R^1CH=CHCH_2Br$ to afford the γ,δ-unsaturated imide 11. Treatment of the latter compound with lithium hydroxide-hydrogen peroxide gives the γ,δ-unsaturated acid 12 which reacts with m-chloroperbenzoic acid to afford the lactone 13 as a mixture of two diastereoisomers arising from the different configurations of the C-O bonds of the two adjoining oxygen-bearing carbon atoms. (The chirality of the R²-bearing carbon atom is conserved.) Protection of the free hydroxyl of 13 (for example by transformation to the corresponding tert-butyldimethylsilyloxy group) and separation by chromatography afford the two diastereoisomers 14 and 15. Subsequent treatment of each of the latter two isomers with lithium hydroxide to open the lactone ring, followed by protection of the resulting nascent hydroxyl (again for example by transformation to the corresponding tert-butyldimethylsilyloxy group) afford the corresponding diol carboxylic acids of formula 2 in which $X^1$ is $OW^a$, $Y^1$ is $OW^b$ and Z is hydrogen and the carbon atoms bearing $X^1$ and $Y^1$ are (R,S) and (S,R), respectively.

Thirdly, with reference to the intermediate of formula 2 required for the preparation of a compound of formula 1 wherein X and Z each is hydroxy and Y is hydrogen, an exemplified preparation of the chirally pure, requisite acids is shown is Scheme 3 wherein $R^1$ and $R^2$ are as defined herein and $OW^a$ and $OW^b$ are joined to form a divalent radical of formula —OC(CH₃)₂O— [i.e. a (1-methylethylidene)-bis(oxy)radical].

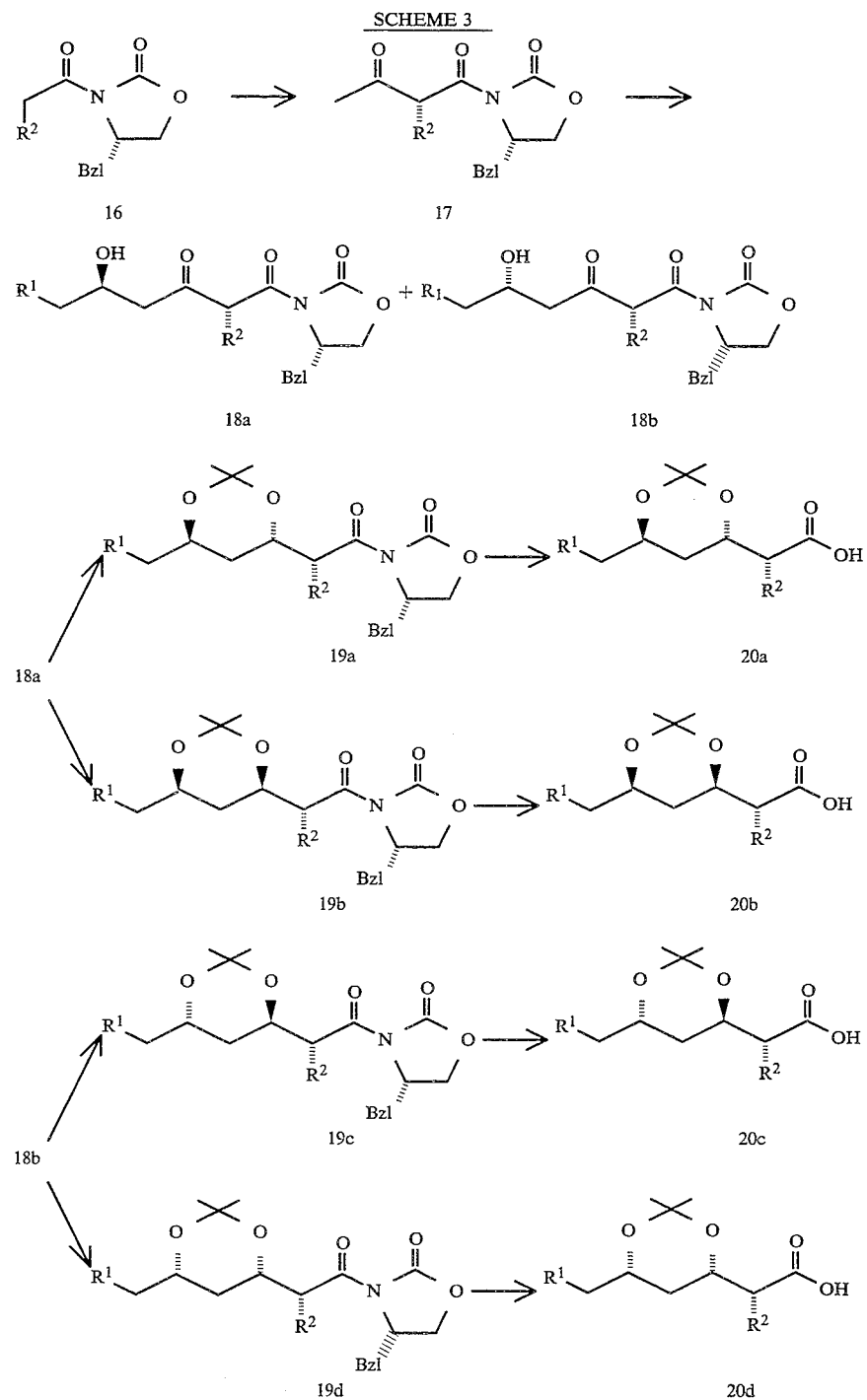

More explicitly, by applying the stereoselective method of D. A. Evans et al., J. Amer Chem. Soc., 104, 1737 (1982), the oxazolidinone auxiliary 16 is alkylated with acetyl chloride to afford the stereochemically homogeneous β-ketoimide 17. The latter compound is subjected to the conditions of an aldol condensation, as described by D. A. Evans et al. J. Amer. Chem. Soc., 112, 866 (1990), whereby it is allowed to react with an aldehyde of formula $R^1CH_2CHO$ in the presence of titanium chloride and diisopropylethylamine to give a mixture of diastereoisomers 18a and 18b. The latter aldol adducts are separated by chromatography and subjected to stereoselective reductions [see D. A. Evans et al., 1990, supra] whereby reduction of 18a or 18b with sodium triacetoxyborohydride and subsequent transformation of the resultant diol system gave respectively the protected diol derivatives 19a and 19c as the preponderant reduction products; and reduction of 18a or 18b with diisobutylaluminum hydride gave respectively the protected diol derivatives 19b and 19c as the preponderant reduction products. In turn, each of the reduction products 19a, 19b, 19c and 19d are transformed to their corresponding protected dihydroxy carboxylic acids of formula 2 (more specifically illustrated in Scheme 3 by formulas 20a, 20b, 20c and 20d) by treatment with lithium hydroxide-hydrogen peroxide.

More particularly, the protected polyhydroxy carboxylic acids of formulae 20a, 20b, 20c and 20d of Scheme 3 are those of formula 2 in which $X^1$ is $OW^a$ and $Z^1$ is $OW^b$ wherein $OW^a$ and $OW^b$ are joined to form a divalent radical —$OC(CH_3)_2O$—, Y is hydrogen and $R^1$ and $R^2$ are as defined herein and the carbon atoms bearing $X^1$ and $Y^1$ have respectively the R and S; R and R; S and R; and S and S configurations.

The starting materials for the preceding processes for preparing the polyhydroxy carboxylic acids of formula 2 are well known or can be prepared by standard methods. For example, methods for preparing the monoprotected diol of formula 5 are described by S. G. Wilkinson in "Comprehensive Organic Chemistry", D. Barton and W. D. Ollis, Eds., Pergamon Press, Oxford, UK, Vol. 1, pp. 662–706, 1979. The oxazolidinone auxiliary 16, used as the starting material for the process depicted by Scheme 3 can be prepared readily by known methods such as described by D. A. Evans et al., 1990, supra, and references therein.

The aminodiols of formula 3 are known having been described by J. R. Luly et al., U.S. Pat. No. 4,845,079, issued Jul. 4, 1989, and by B. Quirico et al., European patent application 332008, published Sep. 13, 1989.

Returning to the key step, the coupling of the appropriate protected polyhydroxy carboxylic acid of formula 2 and the appropriate aminodiol of formula 3 with a coupling agent gives the corresponding protected monoamide of formula 4 which upon deprotection yields the corresponding compound of formula 1.

Biological Aspects

The compounds of formula 1 possess the ability to inhibit renin activity. The renin inhibiting activity of the compounds can be demonstrated in standard pharmacological tests such as those described by M. G. Bock et al., J. Med. Chem., 31, 1918 (1988). As such the compounds are indicated for the diagnosis, prophylaxis and treatment of renin-associated hypertension in mammals including humans, primates, horses and dogs. The compounds also can be used for treating congestive heart failure in mammals including humans, primates, horses and dogs. For the latter purposes or indications, the compounds can be administered orally or parenterally in a vehicle comprising one or more pharmaceutically acceptable carriers, the proportion of which is determined by the solubility and chemical nature of the compound, chosen route of administration and standard biological practice. For oral administration, the compound can be formulated in unit dosage forms such as capsules or tablets each containing a predetermined amount of the active ingredient, ranging from about 25 to 250 mg, in a pharmaceutically acceptable carrier.

For parenteral administration, the compound of formula 1 is administered by either intravenous, subcutaneous or intramuscular injection, in compositions with pharmaceutically acceptable vehicles or carriers. For administration by injection, it is preferred to use the compound in solution in a sterile aqueous vehicle which may also contain other solutes such as buffers or preservatives as well as sufficient quantities of pharmaceutically acceptable salts or of glucose to make the solution isotonic.

Suitable vehicles or carriers for the above noted formulations can be found in standard pharmaceutical texts, e.g. in "Remington's Pharmaceutical Sciences", 18th ed, Mack Publishing Company, Easton, Pa., 1990.

The dosage of the compound will vary with the form of administration and the particular active agent chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the compound is most desirably administered at a concentration level that will lower blood pressure without causing any harmful or deleterious side effects.

For oral administration, the compound is administered in the range of 1.0 to 50 mg per kilogram of body weight per day, with a preferred range of 5 to 30 mg per kilogram.

With reference to systemic administration, the compound of formula 1 is administered at a dosage of 0.1 mg to 5.0 mg per kilogram of body weight per day, although the aforementioned variations will occur. However, a dosage level that is in the range of from about 0.1 mg to 1.0 mg per kilogram of body weight per day is most desirably employed in order to achieve effective results.

The following examples illustrate further this invention. Temperatures are given in degrees Celsius. Solution percentages or ratios express a volume to volume relationship, unless stated otherwise. Nuclear magnetic resonance spectra were recorded on a Bruker 200 MHz or 400 MHz spectrometer (a 400 MHz spectrum being noted as such in its preamble). Abbreviations used in the examples include Boc: t-butyloxycarbonyl; BOP: (benzotriazol-1-yloxy)tris(dimethylamino)phosphonium hexafluorophosphate; Bzl: benzyl; $CH_2Cl_2$, methylenedichloride, DIPEA: diisopropylethylamine; DMF: dimethyl formamide; EtOH: ethanol; EtOAc: ethyl acetate; $Et_2O$: diethyl ether; HOBt: 1-hydroxybenzotriazole; MeOH: methanol, THF: tetrahydrofuran.

EXAMPLE 1

Preparation of (3R, 5S)-5-[1(S)-Benzyloxy-2-phenylethyl]-3-(cyclopropylmethyl)-dihydrofuran-2(3H)-one(9: $R^1$=Ph, $R^2$=cyclopropylmethyl and $W^a$=Bzl)

Under anhydrous conditions, dry dimethylsulfoxide (3.23 mL, 45.5 mmol) was added dropwise over a 10 min period to a stirred solution of oxalyl chloride (2.52 mL, 28.9 mmol) in dry $CH_2Cl_2$ (155 mL) at $-78°$. After another 10 min, a solution of (S)-2-Benzyloxy-3-phenylpropanol (5.00 g, 20.7 mmol) in $CH_2Cl_2$ (52 mL) was added dropwise over 20 min to the preceding solution at $-78°$. [(S)-2-Benzyloxy-3-phenylpropanol is prepared from the commercially available (S)-2-hydroxy-3-phenylpropionic acid by benzylation followed by lithium aluminium hydride reduction.] The resultant mixture was stirred at $-78°$ for 30 min. Thereafter, triethylamine (14.41 mL, 103.3 mmol) was added rapidly to the mixture. The resulting mixture was diluted with $H_2O$ and extracted with EtOAc. The EtOAc extract was washed sequentially with a saturated aqueous solution of $NH_4Cl$, water and brine, dried ($MgSO_4$) and evaporated to dryness to give (S)-2-Benzyloxy-3-phenylpropanal.

The latter aldehyde was dissolved in $Et_2O$ (20 mL). Under anhydrous conditions, the solution of the aldehyde was added dropwise over 15 min to a stirred solution of 3-butenyl magnesium bromide at $-78°$. The latter solution had been prepared by diluting 71 mL of a 0.64M solution of the Grignard reagent in $Et_2O$ with 155 mL of $Et_2O$. After 1 h, the reaction mixture was diluted with $Et_2O$ (100 mL). The resulting mixture was washed with a saturated aqueous solution of $NH_4Cl$ and then with brine. The organic phase was dried ($MgSO_4$) and evaporated to dryness. The residue was purified by chromatography ($SiO_2$, eluent: hexane-EtOAc, 9:1) to give (2S,3S)-2-benzyloxy-1-phenyl-6-hepten-3-ol (4.82 g), $^1H$ NMR ($CDCl_3$) δ 7.25 (m, 10H), 5.75 (m,1H), 4.95 (m,2H), 4.40 (dd,2H), 3.50 (m,2H), 2.90 (m,2H), 2.10 (m,3H), 1.60 (m,2H).

The latter compound (1.96 g, 6.62 mmol) was dissolved in a mixture of acetonitrile, tert-butanol and $H_2O$ (1:1:1, 63 mL) at room temperature (20°–22°). Osmium tetroxide (4.20 mg, 0.02 mmol) and N-methylmorpholine N-oxide.$H_2O$ (1.07 g, 7.95 mmol) were added to the solution. The reaction mixture was stirred for 18 h and then concentrated under reduced pressure. The residue was dissolved in EtOAc (60 mL). The resulting solution was washed with a saturated aqueous solution of sodium bisulfite, water and brine, dried ($MgSO_4$) and evaporated to dryness. The residue was purified by chromatography ($SiO_2$, eluent: MeOH-EtOAc (3:97) to give (2S,3S,6RS)-2-benzyloxy-1-phenyl-3,6,7-heptanetriol (1.78 g), $^1H$ NMR ($CDCl_3$) δ 7.25 (m,10H), 4.40 (dd,2H), 3.50 (m,4H), 2.95 (w,3H), 2.70 (d, 1H), 2.30 (dd, 1H), 1.60 (m,4H).

The latter compound (1.31 g, 0.97 mmol) was dissolved in a mixture of acetonitrile, tert-butanol and $H_2O$ (1:1:1, 39 mL). At 25°, sodium periodate (1.87 g, 8.72 mmol) was added to the solution. The mixture was stirred for 20 win and then diluted with EtOAc. The organic phase was separated and the aqueous phase was extracted with EtOAc. The combined organic phases were washed with brine, dried ($MgSO_4$) and evaporated to dryness. The residue, dissolved in acetone (20 mL), was titrated at 0° with Jones' reagent [A. Bowers et al., J. Chem. Soc., 2555 (1953)]. The mixture was stirred at 25° for 15 win and then concentrated under reduced pressure. The oily residue was purified by chromatography ($SiO_2$, eluent: EtOAc-hexane, 3:7) to give the monosubstituted γ-lactone (5S)-5-[1(S)-benzyloxy-2-phenylethyl]-dihydrofuran-2(3H)-one (881 mg), $^1H$ NMR ($CDCl_3$) δ 7.25 (m,10H), 4.55 (dd,2H), 4.45 (m,1H), 3.60 (ddd,1H), 2.95 (dd,2H), 2.50 (dddd,2H), 2.05 (w,2H), mass spectrum: 331 $(M+H)^+$.

Thereafter the (3R)-3-(2-propenyl) derivative of the latter γ-lactone was prepared as follows: A 1.5M solution of butyllithium in hexane (1.42 mL) was added to a stirred solution of diisopropylamine (340 μL, 2.44 mmol) in THF (10 mL) at $-78°$. After 20 min at $-78°$, a solution of the preceding γ-lactone (450 mg, 1.52 mmol) in THF (1 mL) was added over a 5 min period, keeping the internal temperature of the reaction mixture below $-65°$. After another 20 min at $-78°$, allyl bromide (200 μl, 2.28 mmol) was added dropwise to the mixture. The mixture was stirred at $-78°$ for 2 h. Thereafter, the mixture was quenched with a saturated aqueous solution of $NH_4Cl$ (2 mL). EtOAc (20 mL) was added. The organic phase was separated and the aqueous phase extracted with EtOAc. The combined organic phases were washed with $H_2O$ and brine, dried ($MgSO_4$) and evaporated to dryness. The residue was purified by chromatography ($SiO_2$, eluent: EtOAc-hexane, 1:9) to give the corresponding (3R)-3-(2-propenyl) γ-lactone (386 mg), along with some mixed fractions (63 mg) and starting material (123 mg). The $^1H$ NMR ($CDCl_3$) of the γ-lactone product showed δ 7.25 (m,10H), 5.70 (dddd,1H), 5.05 (m,2H), 4.55 (dd,2H), 4.45 (m,1H), 3.55 (ddd,1H), 2.95 (m,3H), 2.55 (m,1H), 2.05 (m,3H).

Thereafter the latter (3R)-3-(2-propenyl)-γ-lactone was converted to the corresponding (3R)-3-(cyclopropylmethyl)-γ-lactone as follows: The former γ-lactone (148 mg, 0.44 mmol) was dissolved in a cooled (0°) solution of diazomethane (25 mL of a 0.68M solution in $Et_2O$). Palladium acetate (3 mg, 0.01 mL) was added to the cooled solution. After 10 min, the reaction mixture was quenched with acetic acid and then concentrated under reduced pressure. The residue was purified by chromatography ($SiO_2$, eluent: EtOAc-hexane, 1:9) to give (3R,5S)-5-[1(S)-benzyloxy-2-phenylethyl]-3-(cyclopropylmethyl)-dihydrofuran-2(3H)-one (136 mg), $^1H$ NMR ($CDCl_3$) δ 7.25 (m,10H), 4.50 (dd,2H), 4.35 (m,1H), 3.55 (ddd,1H), 2.95 (m,3H), 2.10 (m,2H), 1.50 (m,2H), 0.70 (m,1H), 0.45 (m,2H), 0.10 (m,2H), mass spectrum: 351 $(M+H)^+$.

EXAMPLE 2

Preparation of (2R, 4S, 5S)-N-[1(S)-(Cyclohexylmethyl)-2(R), 3(S)-dihydroxy-5-methylhexyl]-2-(cyclopropylmethyl)-4,5-dihydroxy-6-phenylhexanamide A solution of 2N aqueous sodium hydroxide (178 μL) was added to a stirred solution of the title compound of example 1 (41.5 mg, 0.12 mmol) in methanol (3.5 mL) and $H_2O$ (190 mL). The mixture was stirred briskly at 25° for 2 h. The bulk of the methanol was removed under reduced pressure. After tert-butyldimethylsilyl trifluoromethanesulfonate (407 μL, 1.77 mmol) and 2,6-lutidine (275 μL, 2.36 mmol) had been added thereto, the mixture was stirred at 4° for 18 h. EtOAc (10 mL) was added. The organic phase was separated, washed sequentially with water, a saturated aqueous solution of $NaHCO_3$, 10% (w/v) solution of citric acid in $H_2O$ and brine, dried ($MgSO_4$) and evaporated to dryness. The residue was dissolved in $CH_2Cl_2$ (2 mL) at 25°. DIPEA (41 μL, 0.23 mmol), HOBt (32 mg, 0.24 mmol) and BOP (63 mg, 0.14 mmol) were added to the solution. The resulting mixture was stirred at 25° for 5 min. Thereafter, (2S,3R,4S)-2-amino-1-cyclohexyl-6-methyl-3,4-heptanediol hydrochloride (43 mg, 0.18 mmol, see J. R. Luly et al., U.S. Pat. No. 4,845,079, Jul.

4, 1989) was added and the pH of the reaction mixture was adjusted to 8.0–8.5 with DIPEA. The reaction mixture was stirred at 25° for 3 h and then diluted with EtOAc. The organic phase was separated, washed sequentially with 0.5N aqueous HCl, a saturated aqueous solution of NaHCO$_3$, H$_2$O and brine, dried (MgSO$_4$), and evaporated to dryness. The residue was purified by chromatography. (SiO$_2$, eluent: EtOAc-hexane, 1:9) to give (2R,4S,5S)-5-benzyloxy-4-(tert-butyldimethylsilyloxy)-N-[1(S)-(cyclohexylmethyl)-2(R),3(S)-dihydroxy-5-methylhexyl]-2-(cyclopropylmethyl)-6-phenylhexanamide (53.3 mg), $^1$H NMR (CDCl$_3$) δ 7.25 (m,10H), 5.50 (d,1H), 4.60 (d,1H), 4.35 (m,1H), 4.30 (dd,2H), 3.85 (m, 1H), 3.55 (m,1H), 3.20 (m,1H), 3.00 (m,1H), 2.70–2.30 (m,2H), 2.25–1.80 (m,2H), 1.80–0.7 (m,27H), 0.45 (m,2H), 0.1 (m,2H), 0.1 (s,3H), 0.05 (S,3H).

The latter compound (49.5 mg, 0.07 mmol) was dissolved in THF (1 mL). A 1M solution of tetrabutylammonium fluoride in THF (77 μL, 0.08 mmol) was added to the solution at 25°. The mixture was heated at reflux for 10 min and then allowed to stand at room temperature for 18 h. After the addition of EtOAc (5 mL), the organic phase was washed sequentially with H$_2$O and brine, dried (MgSO$_4$) and evaporated. The residue was purified by chromatography (SiO$_2$, eluent: EtOAc-hexane, 3:7 ) to give the corresponding deprotected γ-hydroxyamide (36.5 mg), mass spectrum: 595 (M+1)$^+$.

The benzyl protective group of the latter compound was removed by subjecting the compound (30 mg, 0.05 mmol) to hydrogenolysis (1 atm of H$_2$, Pd(OH)$_2$/C, EtOH, 18 h). Thereafter, the reaction mixture was filtered through a pad of diatomaceous earth. The pad was washed with EtOH. The combined filtrate and washings were evaporated to dryness. The residue was triturated with Et$_2$O to afford the title compound (18 mg), mass spectrum: 504 (M+1)$^+$ and 526 (M+23)$^+$, $^1$H NMR (CDCl$_3$+1 drop of MeOH) 7.60 (d,1H), 7.20 (m,5H), 4.80 (d,1H), 4.65 (d,1H), 4.40 (d,1H), 4.35 (d,1H), 4.15 (m,1H), 3.65–2.35 (m,7H), 1.90–0.50 (m,27H), 0.45 (m,2H), 0.05 (m,2H).

Alternatively, the title compound was obtained as a separable mixture with its corresponding (2R,4R,5R)-isomer by condensing the (E)-(2R)-2-(cyclopropylmethyl)-6-phenyl-4-hexenoic acid, described in example 3 hereinafter, with the (2S, 3R, 4S)-2-amino-1-cyclohexyl-6-methyl-3,4-heptanediol hydrochloride in the presence of BOP as described in this example to give (E)-(2R)-N-[1(S)-(cyclohexylmethyl)-2(R), 3(S)-dihydroxy-5-methylhexyl]-2-(cyclopropylmethyl)-6-phenyl-4-hexenamide. Subsequent osmium tetroxide-mediated dihydroxylation of the latter heptenamide gave a 7:3 (w/w) mixture of diastereoisomers which were separated by high performance liquid chromatography. The preponderate isomer was the title compound. The mass spectrum of the (2R,4R,5R)-isomer showed 504 (M+1)$^+$.

EXAMPLE 3

Preparation of (3R,5S,1'R)- and (3R,5R, 1'S)-5-[1-(tert-Butyldimethylsilyloxy)-2-phenylethyl]-3-(cyclopropylmethyl)-dihydrofuran-2(3H)-one (14 and 15: R$^1$=Ph, R$^2$=cyclopropylmethyl and W$^a$=tert-butyldimethylsilyl)

A solution of mixed anhydride was prepared by adding pivaloyl chloride (8.34 mL, 67.7 mmol) to a mechanically stirred solution (0°) of 4-pentenoic acid (6.78 g, 67.7 mmol) and triethylamine (11.0 mL, 79 mmol) in THF (100 mL). The solution was stirred at 0° for 1 h and then cooled to −78°.

Another solution was prepared by adding dropwise a 1.6M hexane solution of butyllithium (38.8 mL, 62.1 mmol) to a cooled (−78°) solution of (S)-4-(phenylmethyl)-2-oxazolidinone [10.0 g, 56.4 mmol, described by L. N. Predgen et al., J. Org. Chem., 54, 3231 (1989)] in THF (250 mL). The freshly prepared second solution was kept at −78° for 30 min and then quickly added via a cannula to the solution of mixed anhydride at −78°. The reaction mixture was stirred at −78° for 3 h. Thereafter, H$_2$O (100 mL) and 10% aqueous HCl (50 mL) were added. The resulting mixture was extracted with EtOAc (2×250 mL). The combined extract was washed with a saturated aqueous solution of NaHCO$_3$ and with brine, dried (Na$_2$SO$_4$) and concentrated under reduced pressure. Purification of the residue by flash chromatography (SiO$_2$, eluent: hexane-EtOAc, 15:1) gave (4S)-3-(1-oxo-4-pentenyl)-4-(phenylmethyl)-2-oxazolidinone (10.85 g, 74%) as a colorless oil, $^1$H NMR (CDCl$_3$) δ 7.34–7.2 (m,5H), 6.0–5.8 (m,1H), 5.16–5.0 (m,2H), 4.7 (m,1H), 4.2 (m,2H), 3.3 (dd,J=3.1 Hz,13.2 Hz,1H), 3.1–3.0 (m,2H), 2.75 (dd,J=9.6 Hz,13.3 Hz,1H), 2.5 (m,2H), mass spectrum: 260 (M+H)$^+$.

The latter compound (6.45 g, 24.9 mmol) was dissolved in a cooled (0°) solution of diazomethane (100 mL of 0.6N solution in Et$_2$O). Palladium acetate (280 mg, 1.25 mmol) was added portionwise to the cooled solution. The reaction mixture was stirred at 0° for 1 h.

The mixture was concentrated under reduced pressure. The residue was purified by flash chromatography (SiO$_2$, eluent: hexane - EtOAc,2:1) to give (4S)-3-(3-cyclopropyl-1-oxopropyl)-4-(phenylmethyl)-2-oxazolidinone (4.95 g, 73%) as a white solid, mp 42°–43°.

The latter ozazolidinone derivative was C-alkylated as follows: A 1.6M hexane solution of butyllithium (2.4 mL, 3.84 mmol) was added dropwise to an ice-cold solution of diisopropylamine (0.56 mL, 4.02 mmol) in THF (8 mL). The mixture was stirred at 0° for 15 min, then cooled to −78°. A solution of the last named oxazolidinone derivative (1.00 g, 3.66 mmol) in THF (4 mL) was added to the cooled mixture. After 1 h at −78°, 1,3-dimethyl-3,4,5,6-tetrahydro-2-(1H)-pyrimidinone (0.88 mL, 7.32 mmol) was added, followed by the addition of a solution of (E)-(4-bromo-2-butenyl)benzene (1.15 g, 5.49 mmol) in THF (1.5 mL). [(E)-(4-bromo-2-butenyl)-benzene was prepared in the same manner as described for its cyclohexyl analog by P. Herold et al., J. Org. Chem., 54, 1178 (1989).] The reaction mixture was stirred at −78° for 2 h. Thereafter, it was allowed to warm slowly to 0° C. and stirred for 1 h at that temperature. A saturated aqueous solution of NH$_4$Cl (50 mL) was added and the resultant mixture was extracted with Et$_2$O. The extract was washed serially with 1N aqueous HCl (50 mL), a saturated aqueous solution of NaHCO$_3$ and brine, dried (MgSO$_4$) and then concentrated under reduced pressure. The residue was purified by flash chromatography (SiO$_2$, eluent: hexane-EtOAc, 15:1 then 8:1) to give the oxazolidinone derivative (4S)-3-[(E)-2(R)-(cyclopropylmethyl)-1-oxo-6-phenyl-4-hexenyl]-4-(phenylmethyl)-2-oxazolidinone (1.15 g,78%), $^1$H NMR (CDCl$_3$) δ 7.5–7.1 (m,10H), 5.8–5.5 (m,2H), 4.7 (m,1H), 4.2 (m,2H), 3.4 (d,J=6 Hz,2H), 3.3 (dd,J=3.3 Hz,13.3 Hz,1H), 2.6–2.4 (m,3H), 1.6 (t,J=8.5 Hz,2H), 0.8 (m, 1H) 0.5 (m,2H), 0.1 (m,2H), mass spectrum: 404 (M+H)$^+$.

A 30% aqueous solution of H$_2$O$_2$ (1.0 mL, 8.8 mmol) and a solution of LiOH (166 mg, 396 mmol) in H$_2$O (1.5 mL) were added serially to an ice cold solution of the preceding oxazolidine derivative (1.00 g, 2.48 mmol) in THF/H$_2$O (4:1, 12.5 mL). After 2 h at room temperature, another portion of LiOH (166 mg) was added. The reaction mixture was stirred for 18 h at room temperature. Thereafter, H$_2$O (10 mL) was added to the mixture and the resultant mixture was washed with CH$_2$Cl$_2$. The aqueous layer was rendered acidic with solid citric acid and then extracted with Et$_2$O. The Et$_2$O extract was washed with brine, dried (MgSO$_4$) and concentrated to dryness under reduced pressure to give (E)-(2R)-2-(cyclopropylmethyl)-6-phenyl-4-hexenoic acid (615 mg, 100%) as a colorless oil, $^1$H NMR (CDCl$_3$) 11.9 (broad s,1H), 7.3 (m,5H), 5.8-5.4 (m,2H), 3.4 (d,J=6 Hz,2H), 2.7-2.5 (m, 1H), 2.5-2.2 (m,2H), 1.7-1.4 (m,2H), 0.8 (m, 1H), 0.5 (m,2H), 0.1 (m,2H), mass spectrum: 245 (M+H)$^+$.

m-Chloroperbenzoic acid (630 mg, 2.92 mmol) was added to an ice-cold solution of the latter hexenoic acid (445 mg, 1.82 mmol) in CH$_2$Cl$_2$ (4 mL). The reaction mixture was stirred at 0° for 15 min and then at room temperature for 7 h. After dilution with Et$_2$O, the resultant mixture was washed serially with 5% aqueous Na$_2$S$_2$O$_3$, a saturated aqueous solution of NaHCO$_3$ and brine, dried (MgSO$_4$) and concentrated under reduced pressure. The residue was purified by chromatography (SiO$_2$, eluent: hexane-EtOAc,6:1 then 4:1) to yield (3R,5S,1'R)- and (3R,5R,1'S)-3-(cyclopropylmethyl)-5-(1-hydroxy-2-phenylethyl)-dihydrofuran-2(3H)-one (350 mg, 74%) as a colorless oil, and as a mixture of two diastereoisomers, mass spectrum: 261 (M+H)$^+$.

A solution of the latter mixture of diastereoisomers (475 mg, 1.82 mmol) and 2,6-lutidine (0.64 mL, 5.49 mmol) in CH$_2$Cl$_2$ (7 mL) was cooled to 0°. tert-Butyldimethylsilyl trifluoromethanesulfonate (0.84 mL, 3.66 mmol) was added to the solution. The mixture was stirred at 0° for 15 min and then at room temperature for 15 min. Thereafter, the mixture was diluted with 10% aqueous HCl and extracted with Et$_2$O. The extract was washed with a saturated aqueous solution of NaHCO$_3$ and then with brine, dried (MgSO$_4$), filtered and evaporated to dryness under reduced pressure. The crude residue, a mixture of two diastereoisomers, was purified and separated into the two isomers (noted in the title of this example) by flash chromatography on SiO$_2$.

Elution with hexane-EtOAc (10:1 to 6:1) gave first the less polar (3R,5S,1'R) isomer as a colorless oil [293 mg, 43%, Rf 0.77 (hexane-EtOAc, 2:1), mass spectrum: 375 (M+H)$^+$], and then the more polar (3R,5R,1'S) isomer as a colorless oil [330 mg, 48%, Rf 0.66 (hexane-EtOAc, 2:1), mass spectrum: 375 (M+H)$^+$].

EXAMPLE 4

Preparation of (2R, 4S , 5R)-N-[1(S)-(Cyclohexylmethyl)-2(R), 3(S)-dihydroxy-5methylhexyl]-2-(cyclopropylmethyl)-4,5-dihydroxy-6-phenylhexanamide (a) A mixture of the title (3R,5S,1'R) isomer of example 3 (138 mg, 0.37 mmol) and LiOH.H$_2$O(62 mg, 1.48 mmol) in THF (2 mL) and H$_2$O (0.5 mL) was stirred at room temperature for 18 h. The mixture was concentrated under reduced pressure. Traces of water were removed from the residue by dissolving it serially in benzene and toluene and evaporating the resulting solutions. tert-Butyldimethylsilyl trifluoromethanesulfonate (1.27 mL, 5.53 mmol) was added to an ice-cold solution of the residue and 2,6-lutidine (0.86 mL, 7.38 mmol) in CH$_2$Cl$_2$ (1.5 mL) and DMF (1.5 mL). The mixture was stirred at room temperature for 18 h. Thereafter, the mixture was diluted with EtOAc(15 mL), washed serially with a cold 10% aqueous solution of citric acid (2×5 mL), a saturated aqueous solution of NaHCO$_3$ (10 mL) and brine (10 mL), dried (MgSO$_4$) and concentrated under reduced pressure. A mixture of the resulting residue and K$_2$CO$_3$ (51 mg, 0.37 mmol) in MeOH/THF/H$_2$O (3:1:1, 5 mL) was stirred at room temperature for 6.5 h, an additional amount (26 mg) of K$_2$CO$_3$ being added after 4 h. The mixture was diluted with EtOAc and brine, and rendered acidic by the addition of a cold aqueous solution of citric acid. The organic phase was separated, washed with brine, dried (MgSO$_4$) and concentrated under reduced pressure. The residue was purified by flash chromatography (SiO$_2$, eluent: hexane-EtOAc, 6:1) to yield (2R,4S,5R)-4,5-di(tert-butyldimethylsilyloxy)-2-(cyclopropylmethyl)-6-phenylhexanoic acid (180 mg, 96%) as a colorless oil, $^1$H NMR(CDCl$_3$) δ 7.5 (m,5H), 4.1(t,J=4.5 Hz, 1H), 3.95 (d,J=6 Hz,1H), 3.0 (d,J=6 Hz,3H), 2.15 (t,J=7 Hz,1H), 2.0-1.7 (m, 3H), 1.6 (m, 1H), 1.2 (s, 9H), 1.1 (s,9H), 1.05 (m, 1H), 0.75 (m,2H), 0.55 (s,3H), 0.5 (m,2H), 0.3 (s,3H), 0.2 (s, 3H), −0.05 (s,3H).

(b) A solution of the latter compound (170 mg, 0.33 mmol),BOP (178 mg, 0.40 mmol) and HOBt (54 mg, 0.40 mmol) in DMF (2 mL) was cooled to 0°. A solution of (2S,3R,4S)-2-amino-1-cyclohexyl-6-methyl-3,4-heptanediol hydrochloride, (123 mg, 0.44 mmol) and DIPEA (0.21 mL, 1.20 mmol) in DMF(1.5 mL) was added to the cooled solution. The mixture was stirred at room temperature for 1.5 h, diluted with EtOAc, washed serially with 10% aqueous HCl, a saturated solution of NaHCO$_3$ and brine, dried (MgSO$_4$) and concentrated to dryness. The residue was purified by flash chromatography. (SiO$_2$, eluent: hexane-EtOAc, 6:1) to give (2R,4S,5R)-4,5-di(tert-butyldimethylsilyloxy)-N-[1(S)-(cyclohexylmethyl)-2(R),3(S)-dihydroxy-5-methylhexyl]-2-(cyclopropylmethyl)-6-phenylhexanamide (180 mg, 74%) as colorless oil, $^1$H NMR(CDCl$_3$) δ 7.5 (m,5H), 5.7 (d, J=8.5 Hz,1H), 4.9 (s,1H), 4.7 (m, 1H), 4.1 (t, J=7 Hz,1H), 3.85 (m, 1H), 3.6 (m,2H), 3.1 (m,2H), 2.7 (m, 1H), 2.25 (m,2H), 2.2-1.4 (m, 15H), 1.3 (d, J=7 Hz,3H), 1.28 (s,9H), 1.25 (d, J=7 Hz,3H), 1.2 (s,9H), 1.1 (m,1H), 0.9 (m,2H), 0.45 (s,3H), 0.4 (s,3H), 0.3 (m,2H), 0.25 (s,3H), −0.05 (s,3H).

(c) The latter compound (164 mg, 0.23 mmol) was dissolved in a mixture of 40% aqueous HF and acetonitrile (1:19, 3 mL). The solution was stirred at room temperature for 1 h, diluted with EtOAc, washed with a saturated aqueous solution of NaHCO$_3$ and then brine, dried (MgSO$_4$) and concentrated to dryness under reduced pressure. The residue was purified by flash chromatography (SiO$_2$, eluent: hexane-EtOAc-EtOH,15:10:1) to give an oil which on trituration with Et$_2$O yielded the title compound of this example as a white solid, $^1$H NMR (CDCl$_3$) δ 7.2 (m,5H), 4.9 (broad s,1H), 4.4 (m, 1H), 4.2 (d, J =7 Hz,1H), 3.7 (m, 1H), 3.5 (m, 1H), 3.2 (m,2H), 2.9 (dd, J=3.1 Hz,13.2 Hz,1H), 2.6 (m,2H), 2.0-1.55 (m,11H), 1.55-1.05 (m,8H), 0.9 (d, J=7 Hz,3H), 0.8 (d, J=7 Hz,3H), 0.8 (m, 1H), 0.5 (m,2H), 0.1 (m,2H), mass spectrum: 504 (M+H)$^+$.

EXAMPLE 5

Preparation of (2R, 4R, 5S)-N-[1(S)-(Cyclohexylmethyl)-2(R), 3(S)-dihydroxy-5-methylhexyl]-2-(cyclopropylmethyl)-4,5-dihydroxy-6-phenylhexanamide By following the procedure of sections (a) and (b) of example 4 but replacing the (3R,5S,1′R) isomer of example 3 with the title (3R,5R,1′S) isomer of example 3, (2R,4R,5S)-4,5-di(tert-butyldimethylsilyloxy)-N-[1(S)-(cyclohexylmethyl)-2(R),3(S)-dihydroxy-5-methylhexyl]-2-(cyclopropylmethyl)-6-phenylhexanamide was obtained as a white solid, mass spectrum: 732 (M+H)+.

The latter compound (164 mg, 0.23 mmol) was dissolved in THF (2 mL). The solution was stirred with a 1M THF solution of tetrabutylammonium fluoride (0.68 mL) at room temperature. After 5 h, another 0.68 mL portion of the tetrabutylammonium fluoride solution was added and the resultant mixture was stirred for 18 h. The mixture was evaporated to dryness. The residue was purified by flash chromatography (SiO$_2$, eluent: hexane-EtOAc-EtOH,15:10:2) to give the title compound of this example as a white solid (114 mg, 100%). The solid was purified further by trituration with Et$_2$O, $^1$H NMR (CDCl$_3$) δ 7.3 (m,5H), 5.9 (d, J=8.8 Hz,1H), 4.5–4.3 (m, 2H), 3.85–3.6 (m,2H), 3.4–3.2 (m,2H), 2.9 (dd, J=3.3 Hz,12.5 Hz,1H), 2.7 (g, 1H), 2.5 (m, 1H), 2.1–1.5 (m,11H), 1.5–1.1 (m,7H), 1.0 (d, J=7 Hz,3H), 0.9 (d, J=7 Hz,3H), 0.8 (m, 1H), 0.5 (m,2H), 0.1 (t, J=7 Hz,2H), mass spectrum: 504 (M+H)+.

EXAMPLE 6

Preparation of (4S)-3-[2(R)-(Cyclopropylmethyl)-1,3-dioxobutyl]-4-(phenylmethyl)-2-oxazolidinone (17, R$^2$=cyclopropylmethyl)

Under a nitrogen atmosphere, a solution of the (4S)-3-(3-cyclopropyl-1-oxopropyl)-4-(phenylmethyl)-2-oxazolidinone (6.01 g, 22.0 mmol, described in example 3) in anhydrous THF (10 mL) was added to a cold (−78°) stirred solution of lithium diisopropylamide (963 mg, 9.0 mmol) in anhydrous THF (10 mL). The mixture was stirred at −78° for 45 min and then transferred by cannula into a cold (−78°) solution of acetyl chloride (0.86 mL, 12 mmol) in anhydrous THF (5 mL). The resultant mixture was stirred for 15 min at −78° C., then quenched with a saturated aqueous solution of NH$_4$Cl, allowed to warm to room temperature (20°–22°) and diluted with Et$_2$O. The layers were separated and the aqueous phase was extracted with Et$_2$O.

The combined organic phases were washed with brine, dried (MgSO$_4$) and concentrated to dryness. The residue was purified by flash chromatography (SiO$_2$, eluent: hexane-EtOAc, 4:1) to give the title compound as a clear oil (2.11 g, 83%), $^1$H NMR (400 MHz, CDCl$_3$) δ 0.14 (m,2H), 0.51 (m,2H), 0.88 (m, 1H), 1.55 (m, 1H), 2.10 (m, 1H), 2.77 (dd,J=9.9 Hz,13.6 Hz, 1H), 3.43 (dd,J=3.3 Hz,13.6 Hz,1H), 4.20 (m,2H), 4.68 (m,2H), 7.25–7.38 (m,5H) mass spectrum (chemical ionization, NH$_3$): 316 (M+H)+, 333 (M+NH$_4$)+.

EXAMPLE 7

Preparation of (4S,2′R,5′R)- and (4S,2′R,5′S)-3-[2-(Cyclopropylmethyl)-5-hydroxy-1,3-dioxo-6-phenylhexyl]-4-(phenylmethyl)-2-oxazolidinone (18a, R$^1$=phenyl and R$^2$=cyclopropylmethyl, and 18b, R$^1$=phenyl and R$^2$=cyclopropylmethyl, respectively)

Under a nitrogen atmosphere, the title compound of example 6 (1.00 g, 3.17 mmol) was dissolved in anhydrous CH$_2$Cl$_2$ (25 mL). The solution was cooled (−15°). A 1.0M CH$_2$Cl$_2$ solution of TiCl$_4$ (4.2 mL, 4.19 mmol) and DIPEA (0.73 mL, 4.19 mmol) were added to the cooled solution. The mixture was stirred at −15° C. for 1 h and then cooled to −78°. Freshly distilled phenylacetaldehyde (0.50 mL, 4.19 mmol) in CH$_2$Cl$_2$ (2 mL) was added slowly and the resultant mixture was stirred for 1 h at −78° C. Thereafter, the mixture was quenched with NH$_4$Cl buffer (pH=7), diluted with CH$_2$Cl$_2$ and allowed to warm to room temperature over 30 min. The layers were separated and the aqueous layer was extracted with CH$_2$Cl$_2$. The combined organic layers were washed with brine, dried (MgSO$_4$) and concentrated to dryness. The residue was purified by flash chromatography (SiO$_2$, eluent: hexane-EtOAc, 4:1) to give a mixture of the title isomers (1.13 g, 82%, ratios of isomers: 67:33, respectively). The isomers were separated by reversed phase HPLC; for the first mentioned title compound, $^1$H NMR(200 MHz, CDCl$_3$) δ 0.10 (m,2H), 0.48 (m,2H), 0.81 (m, 1H), 1.52 (m, 1H), 2.10 (m, 1H), 2.60–3.09 (m,6H), 3.40 (dd,J=13.8 Hz,3.6 Hz,1H), 4.05–4.85 (m,5H), 7.05–7.50 (m, 10H) ; for the second mentioned title compound $^1$H NMR (400 MHz, CDCl$_3$) δ 0.11 (m,2H),0.48 (m,2H), 0.82 (m, 1H), 1.48 (m, 1H), 2.08 (m, 1H), 2.69–2.80 (m, 5H) , 2.92 (m, 1H) , 3.38 (dd,J=4.0 Hz,14.5 Hz,1H), 4.28 (m,2H), 4.39 (m, 1H), 4.56 (m, 1H), 4.67 (m, 1H) , 7.18–7.38 (m, 10H).

EXAMPLE 8

Preparation of Diastereoisomers of 3-[2-(Cyclopropylmethyl)-3,5-[1-methylethylidene)bis(oxy)]-1-oxo-6-phenylhexyl]-4-(phenylmethyl)-2-oxazolidinone The following oxazolidinone diastereoisomers were prepared by stereoselective reduction of the title compounds of example 7, followed by protection of the resultant 1,3-diol systems in the form of an acetonide.

(a) (4S,2′R,3′R,5′S)-isomer (19c, R$^1$=phenyl and R$^2$=cyclopropylmethyl): Sodium triacetoxyborohydride (589 mg, 2.78 mmol) was added to a solution of the title (4S,2′R,5′S)-isomer of example 7 (603 mg, 1.39 mmol) in acetic acid (15 mL). The mixture was stirred at room temperature for 3 h. The solvent was removed and the residue was suspended in a saturated aqueous solution of NaHCO$_3$. The suspension was extracted with EtOAc. The extract was washed with brine, dried (MgSO$_4$) and concentrated. The residue was dissolved in dimethylformamide/2,2-dimethoxypropane (10 mL, 1:1). A catalytic amount of p-toluenesulfonic acid was added to the solution. The resulting mixture was stirred at room temperature for 18 h. Thereafter, the mixture was quenched with 0.5N aqueous HCl and diluted with Et$_2$O. The aqueous layer was separated and extracted with Et$_2$O. The combined organic extracts were washed with brine, dried (MgSO$_4$) and concentrated to dryness to give a mixture of the target isomer and the corresponding (4S,2′R,3′S,5′S)-isomer (481 mg, 73%, ratio of isomers: 87:13, respectively). The isomers were separated by flash chromatography (SiO$_2$, eluent: hexane-EtOAc, to 9:1) give the target (4S,2′R,3′R,5′S)-isomer of the title compound (420 mg, 63%) $^1$H NMR (400 MHz, CDCl$_3$) δ 0.00 (m,2H), 0.38 (m,2H), 0.72 (m, 1H), 1.25 (s,3H), 1.31 (s,3H), 1.65 (m,3H), 2.68 (dd,J=6.2 Hz,13.8 Hz,1H), 2.88 (m,2H), 3.15 (dd,J=3.3 Hz,13.6 Hz,1H), 4.12 (m,4H), 4.28 (m, 1H), 4.78 (m, 1H), mass spectrum: 478 (M+H)+, 500(M+Na)+.

(b) (4S,2′R,3′S,5′R)-isomer (19a, R$^1$=phenyl and R$^2$=cyclopropylmethyl): The title (4S,2′R,5′R)-isomer of example 7 (208 mg, 0.48mmol) was reduced and the resultant diol system was protected in the same manner as described in section (a) of this example to give a mixture of the target isomer and the corresponding (4S,2′R,3′R,5′R)-isomer (ratio of isomers: 82:18, respectively). Separation of the isomers by flash chromatography (SiO₂, eluent: hexane-EtOAc, 9:1) gave the target (4S,2'R,3'S,5'R)-isomer of the title compound (93 mg, 41%), ¹H NMR (400 MHz, CDCl₃) δ 0.04 (m, 2H), 0.37 (m,2H), 0.67 (m, 1H), 1.31 (s,3H), 1.38 (s,3H), 1.51 (m, 1H), 1.69 (m,2H), 1.81 (m, 1H), 2.51 (dd,J=10 Hz,14 Hz,1H), 2.67 (dd,J=6.6 Hz, 13.7 Hz,1H), 2.93(dd,J=7.0 Hz,13.3 Hz,1H), 3.22 (dd,J=3.3 Hz,13.3 Hz,2H), 4.11 (m,4H), 4.25 (m, 1H), 4.68 (m, 1H), 7.25-7.35 (m, 10H), mass spectrum: 478 (M+H)⁺, 500 (M+Na)⁺.

(c) (4S,2'R,3'S,5'S)-isomer (19d, R¹=phenyl and R²=cyclopropylmethyl): Under a nitrogen atmosphere, a 1.0M hexane solution of diisobutylaluminum hydride (5.0 mL) was added to a cold (−78°) stirred solution of the title (4S,2'R,5'S)-isomer of example 7 (72 mg, 0.16 mmol) in anhydrous THF (5 mL). The reaction mixture was stirred at −78° for 4 h. Thereafter, the mixture was quenched with a saturated aqueous solution of NH₄Cl, diluted with EtOAc and allowed to warm to room temperature over 1 h. The layers were separated and the aqueous layer was extracted with EtOAc. The combined organic layers were washed with brine, dried (MgSO₄) and concentrated to dryness. The residue was dissolved in dimethylformamide/2,2-dimethoxypropane (2.0 mL, 1:1). A catalytic amount of p-toluenesulfonic acid was added to the solution. The resulting mixture was stirred at room temperature for 18 h. Thereafter, the reaction was worked up in the same manner as described in section (a) of this example to give the target isomer and the corresponding (4S,2'R,3'R,5'S)-isomer (63 mg, ratio of isomers: 67:33, respectively). Separation of the isomers by flash chromatography (SiO₂, eluent: hexane-EtOAc, 9:1) gave the target (4S,2'R,3'S,5'S)-isomer of the title compound (42 mg, 54%), ¹H NMR (400 MHz, CDCl₃) δ 0.05 (m,2H), 0.35 (m,2H), 0.67 (m, 1H), 1.39 (s,3H), 1.43 (s,3H), 1.50 (m,2H), 1.79 (m, 1H), 2.55 (m,2 h), 2.95 (dd,J=5.2 Hz,14.0 Hz,1H), 3.17 (dd,J=3.6 Hz,13.6 Hz,1H), 4.05 (m,2H), 4.14 (d,J=6.0 Hz,2H), 4.21 (m, 1H), 4.68 (m, 1H), 7.18-7.40 (m, 10H), mass spectrum: 478 (M+H)⁺, 500 (M+Na)⁺.

(d) (4S,2'R,3'R,5'R)-isomer (19b, R¹=phenyl and R²=cyclopropylmethyl): The title (4S,2'R,5'R)-isomer of example 7 (131 mg, 0.30 mmol) was reduced and the resultant diol system was protected in the same manner as described in section (c) of this example to give a mixture of the target isomer and the corresponding (4S,2'R,3'S,5'R)-isomer (ratio of isomers: 75:25, respectively). Separation of the isomers by flash chromatography (SiO₂, eluent: hexane-EtOAc, 9:1) gave the target (4S,2'R,3'R,5'R)-isomer of the title compound (50 mg, 35%), ¹H NMR (400 MHz, CDCl₃) δ 0.00 (m,2H), 0.35 (m,2H), 0.69 (m, 1H), 1.30 (m, 1H), 1.37 (s,3H), 1.41 (s,3H), 1.55 (m,1H), 2.65 (dd,J=7.3 Hz,13.5 Hz,2H), 2.80 (dd,J=8.9 Hz,13.6 Hz, 1H), 2.95 (dd,J=5.8 Hz,14.0 Hz,1H), 3.18 (dd,J=3.2 Hz, 13.6 Hz,1H), 4.05 (m, 1H), 4.13 (m,2H), 4.28 (m, 1H), 4.76 (m, 1H), 7.18-7.38 (m, 10H), mass spectrum: 478 (M+H)⁺, 500 (M+Na)⁺.

EXAMPLE 9

Preparation of Diastereoisomers of 2-(Cyclopropylmethyl)-3,5-[(methylethylidene)bis(oxy)]-6-phenylhexanoic acid The following procedure was used to transform the chirally pure oxazolidinone diastereoisomers of example 8 into the corresponding protected dihydroxy carboxylic acids.

The appropriate isomer of example 8 was dissolved in H₂O/THF (1:3). The solution was cooled to 0°. A 30% aqueous solution of H₂O₂ (5 equiv.) and an aqueous solution of LiOH (2 equiv.) were added serially to the stirred cooled solution. The mixture was allowed to warm to room temperature and then stirred for 4 h. Thereafter, the reaction mixture was quenched with a 1.5M aqueous solution of Na₂S₂O₃, concentrated under reduce pressure to remove THF and then rendered basic (pH>11) by the addition of a saturated aqueous solution of NaHCO₃. The aqueous mixture was extracted with CH₂Cl₂ and then rendered acidic (pH<3) by the addition of 2N aqueous HCl. The acidified mixture was extracted with EtOAc. The EtOAc extract was washed with brine, dried (MgSO₄) and concentrated to dryness to yield the desired protected dihydroxy carboxylic acid, which was used for the next step without purification.

EXAMPLE 10

Preparation of (2R,3S,5R)-N-[1(S)-(Cyclohexylmethyl)-2(R), 3(S)-dihydroxy-5-methylhexyl]-2-(cyclopropylmethyl)-3,5-dihydroxy-6-phenylhexanamide A solution of the preceding protected dihydroxy carboxylic acid (20 mg, 0,063 mmol, derived from the (4S,2'R,3'S,5'R)-isomer of example 8b, DIPEA (0,04 mL, 0.19 mmol) and BOP (31 mg, 0.07 mmol) was stirred at room temperature for 5 min. (2S,3R,4S)-2-amino-1-cyclohexyl-6-methyl-3,4-heptanediol hydrochloride (24 mg, 0.07 mmol) was added to the mixture. The resulting mixture was stirred at room temperature for 1 h, diluted with EtOAc and quenched with 0.5N aqueous HCl. The layers were separated. The aqueous layer was extracted with fresh EtOAc. The combined organic layers were washed with brine, dried (MgSO₄) and concentrated to dryness. The residue was dissolved in a mixture of MeOH and H₂O. A strongly acidic, gel-type ion exchange resin (Amberlite IR-120 °) was added to the solution. The mixture was heated at 60° C. for 4 h, cooled and filtered. The filtrate was concentrated to dryness. The residue was purified by flash chromatography (SiO₂, eluent: hexane-EtOAc, 1:1) to give the title compound, ¹H NMR (400 MHz, CD₃OD) δ 0.0 (m,2H), 0.32 (m,2H), 0.55 (m, 1H), 0.77 (m, 10H), 0.98-1.80 (m,20H), 2.25 (m, 1H), 2.65 (d,J=7.0 Hz,2H), 3.00 (d,J=10.0 Hz,2H), 3.91 (m,2H), 4.28 (m, 1H), 7.01-7.19 (m,6H), mass spectrum: 504 (M+H)⁺, 526 (M+Na)⁺.

EXAMPLE 11

Preparation of (2R,3R,5R)-N-[1(S)-(Cyclohexylmethyl)-2(R),3(S)-dihydroxy-5-methylhexyl]-2-(cyclopropylmethyl)-3,5-dihydroxy-6-phenylhexanamide By following the procedure of example 10, but using instead the protected dihydroxy carboxylic acid (23 mg, 0,073 mmol) derived from the (4S,2'R,3'R,5'R)-isomer of example 8d, the title compound (14 mg, 39%) was obtained, H¹ NMR (400 MHz, CDCl₃+1 drop of CD₃OD) δ 0.05 (m,2H), 0.35 (m,2H), 0.58 (m, 1H), 0.70-0.95 (m, 10H), 1.00-1.90 (m,20H), 2.18 (m, 1H), 2.70 (m, 1H), 3.05 (m, 1H), 3.25 (m,2H), 3.90 (m,2H), 4.15 (m, 1H), 6.81 (m, 1H), 7.04-7.21 (m,5H); mass spectrum: 504 (M+H)⁺.

EXAMPLE 12

Preparation of (2R, 3R, 5S)-N-[1(S)-(Cyclohexylmethyl)-2(R), 3(S)-dihydroxy-5-methylhexyl]-2-(cyclopropylmethyl)-3,5-dihydroxy-6-phenylhexanamide By following the procedure of example 10, but using instead the protected dihydroxy carboxylic acid (20 mg, 0,063 mmol) derived from the (4S,2′R,3′R,5′S)-isomer of example 8a, the title compound (21 mg, 68%) was obtained, $H^1$ NMR (400 MHz, $CDCl_3$+1 drop of $CD_3OD$) δ 0.05 (m,2H), 0.38 (m,2H), 0.60 (m, 1H), 0.65–0.95 (m,9H), 0.95–1.90 (m,20H), 2.22 (m, 1H), 3.05 (m, 1H), 3.19 (m, 1H) 3.95 (m,2H), 4.18 (m, 1H), 6.68 (d,J=11.0 Hz,1H), 7.05–7.20 (m,5H).

EXAMPLE 13

Preparation of (2R, 3S, 5S)-N-[1(S)-(Cyclohexylmethyl)-2(R), 3(S)-dihydroxy-5-methylhexyl]-2-(cyclopropylmethyl)-3,5-dihydroxy-6-phenylhexanamide By following the procedure of example 10, but using instead the protected dihydroxy carboxylic acid (12 mg, 0,038 mmol) derived from the (4S,2′R,3′S,5′S)-isomer of example 8c, the title compound (21 mg, 68%) was obtained, $H^1$ NMR (400 MHz, $CDCl_3$) δ 0.05 (2H,m), 0.38 (2H,m), 0.57 (1H,m), 0.80–1.02 (m,8H), 1.08–2.20 (m,22H), 3.20–3.35 (m,2H), 3.88 (s,2H), 4.30 (1H,m), 4.51 (1H,m), 6.27 (d, 1H), 6.65 (d,J=8.1 Hz,2H), 6.86 (t,J=7.2 Hz,1H), 7.28–7.38 (m,3H), mass spectrum: 504.4 $(M+H)^+$.

EXAMPLE 14

Plasma Renin Assay

The ability of the compounds of formula 1 to inhibit human renin can be demonstrated in the plasma renin assay. The assay is performed as follows: The test compound (i.e. the inhibitor) is dissolved in dimethylsulfoxide(1 mM stock solution) and diluted with an aqueous buffer solution of 270 mM 2-(N-morpholino)ethanesulfonic acid and 1% human serum albumin (pH 5.85, also containing dimercaprol and 8-hydroxyquinoline sulfate in accordance with the instructions of the RIA kit noted below) to give an assay mixture in which the final dimethylsulfoxide content is 1% (v/v).

A human plasma pool is used as the source of both the substrate (angiotensinogen) and the enzyme (renin). The reaction is initiated by the addition of 50 μL of human plasma pool to 50 μL of various concentrations of inhibitor in the 1% dimethylsulfoxide assay buffer. The plasma renin activity is measured by the amount of angiotensin I generated at pH 6.0 following a 2 h incubation at 37°.

Quantitation of angiotensin I is performed by radioinununoassay (RIA kit from New England Nuclear-Dupont, Mississauga, ON, Canada). The enzymatic activity of renin is expressed in ng of angiotensin I generated/mL/2 h. The extent of inhibition of the reaction is determined from the amount of angiotensin I generated in reference to a control prepared without inhibitor. Nonlinear regression analysis is used to calculate the $IC_{50}$ values, i.e. the molar concentration of the test compound required to cause a 50% inhibition of the enzyme activity.

The compounds of formula 1 exhibited $IC_{50}$'s in the range of $10^{-6}$ to $10^{-9}$ molar in this assay. The following table exemplifies results obtained for compounds of formula 1.

TABLE

| COMPOUND OF FORMULA 1 | $IC_{50}$ (nM) |
| --- | --- |
| Title compound of example 2 | 22 |
| Corresponding (2R,4R,5R)-isomer of title compound of example 2 | 38 |
| Title compound of example 4 | 110 |
| Title compound of example 5 | 48 |
| Title compound of example 10 | 21 |
| Title compound of example 11 | 260 |
| Title compound of example 12 | 1000 |
| Title compound of example 13 | 175 |

Other examples of compounds of formula 1 are: the [2R,4R,5R,N-(1S,2R,3S)]-isomer wherein $R^1$ is phenyl, $R^2$ is 4-imidazolylmethyl, $R^3$ is cyclohexylmethyl, $R^4$ is 2-methylpropyl, X and Y each is hydroxy and Z is hydrogen ($IC_{50}$=173 nM), the [2S,4S,5S,N-(1S,2R,3S)]-isomer wherein $R^1$ is phenyl, $R^2$ is 2-thienylmethyl, $R^3$ is cyclohexylmethyl and $R^4$ is 2-methylpropyl, X and Y each is hydroxy and Z is hydrogen ($IC_{50}$=485 nM), the [2R,4S,5S,N-(1S,2R,3S)]-isomer wherein $R^1$ is phenyl, $R^2$ is 2-methyl-4-thiazolylmethyl, $R^3$ is cyclohexylmethyl, $R^4$ is 2-methylpropyl, X and Y each is hydroxyl and Z is hydrogen ($IC_{50}$=220 nM), the [2R,4S,5S,N-(1S,2R,3S)]-isomer wherein $R^1$ is 1-naphthyl, $R^2$ is cyclopropylmethyl, $R^3$ is cyclohexylmethyl, $R^4$ is 2-methylpropyl, X and Y each is hydroxy and Z is hydrogen.

Still other examples of compounds of formula 1 in which X and Y each is hydroxyl and Z is hydrogen are:
the [2R,4S,5S,N-(1S,2R,3S)]-isomer wherein $R^1$ is phenyl, $R^2$ is 4-thiazolylmethyl, $R^3$ is phenylmethyl and $R^4$ is 2-methylpropyl,
the [2R,4R,5R,N-(1S,2R,3S)]-isomer wherein $R^1$ is phenyl, $R^2$ is 2-amino-4-thiazolylmethyl, $R^3$ is cyclohexylmethyl and $R^4$ is 2-methylpropyl,
the [2R,4R,5R,N-(1S,2R,3S)]-isomer wherein $R^1$ is 1-naphthyl, $R^2$ is cyclopropylmethyl, $R^3$ is cyclohexylmethyl and $R^4$ is 2-methylpropyl,
the [2R,4S,5R,N-(1S,2R,3S)]-isomer wherein $R^1$ is 4-hydroxyphenyl, $R^2$ is 4-thiazolylmethyl, $R^3$ is cyclopropylmethyl and $R^4$ is 2-methylpropyl,
the [2R,4R,5R,N-(1S,2R,3S)]-isomer wherein $R^1$ is 4-methoxyphenyl, $R^2$ is cyclopentylmethyl, $R^3$ is cyclohexylmethyl and $R^4$ is propyl,
the [2R,4R,5R,N-(1S,2R,3S)]-isomer wherein $R^1$ is butyl, $R^2$ and $R^3$ each is cyclohexylmethyl and $R^4$ is 2-methylpropyl, and
the [2R,4R,5S,N-(1S,2R,3S)]-isomer wherein $R^1$ is 2-fluorophenyl, $R^2$ is propyl and $R^3$ and $R^4$ each is 2methylpropyl.

Still other examples of compounds of formula 1 in which X and Z each is hydroxyl and Y is hydrogen are:
the [2R,3S,5S,N-(1S,2R,3S)]-isomer wherein $R^1$ is phenyl, $R^2$ is cyclopentylmethyl, $R^3$ is cyclohexylmethyl and $R^4$ is cyclopropyl,
the [2R,3R,5R,N-(1S,2R,3S)]-isomer wherein $R^1$ is cyclopentyl, $R^2$ and $R^3$ each is cyclopentylmethyl and $R^4$ is 2-methylpropyl,
the [2R,3R,5R-N-(1S,2R,3S)]-isomer wherein $R^1$ is 2naphthyl, $R^2$ is 4-thiazolylmethyl, $R^3$ is benzyl and $R^4$ is 2-methylpropyl,
the [2R,3S,5S,N-(1S,2R,3S)]-isomer wherein $R^1$ is 1naphthyl, $R^2$ is 3-methylbutyl, $R^3$ is cyclohexylmethyl and $R^4$ is 2-methylpropyl,
the [2R,3R,5R,N-(1S,2R,3S)]-isomer wherein $R^1$ is 4-chlorophenyl, $R^2$ is 4-imidazoylmethyl, $R^3$ is cyclohexylmethyl and $R^4$ is cyclohexyl, the [2R,3S,5S,N-(1S,2R,3S)]-isomer wherein $R^1$ is 3-methoxypropyl, $R^2$ is cyclopropylmethyl, $R^3$ is (4-methoxyphenyl)methyl, and $R^4$ is 2-methylpropyl, the [2R,3S,5S,N-(1S,2R,3S)]-isomer wherein $R^1$ is phenyl, $R^2$ is benzyl, $R^3$ is cyclohexylmethyl and $R^4$ is cyclopropyl, and the [2R,3S,5R,N-(1S,2R,3S)]-isomer wherein $R^1$ is 4methoxyphenyl, $R^2$ is cyclopropylmethyl, $R^3$ is benzyl and $R^4$ is 2-methylpropyl.

The embodiments of this invention in which an exclusive property or privilege is claimed as defined as follows:

1. A compound of formula 1

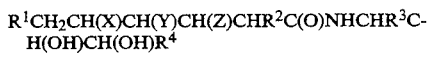

$$R^1CH_2CH(X)CH(Y)CH(Z)CHR^2C(O)NHCHR^3CH(OH)CH(OH)R^4 \quad 1$$

wherein $R^1$ is phenyl, 4-hydroxyphenyl, 4-methoxyphenyl, 2-fluorophenyl or 1-naphthyl;

$R^2$ is cyclopropylmethyl, cyclopentylmethyl, cyclohexylmethyl, benzyl, 4-imidazolylmethyl, 2-thienylmethyl, 4-thiazolymethyl, 2-methyl-4-thiazolylmethyl or 2-amino-4thiazolylmethyl;

$R^3$ is 2-methylpropyl, cyclopropylmethyl, cyclohexylmethyl or benzyl;

$R^4$ is lower alkyl or lower cycloalkyl; and

X and Y each is hydroxy and Z is hydrogen or X and Z each is hydroxy and Y is hydrogen, with the provisos that (a) the carbon atom bearing $R^2$ has the (R) configuration except when $R^2$ is 2-thienylmethyl, X and Y each is hydroxy and Z is hydrogen, then the carbon atom bearing the $R^2$ has the (S) configuration; (b) the carbon atoms bearing $R^3$ and $R^4$ each has the (S) configuration; and (c) the carbon atom located between the latter two carbon atoms has the (R) configuration.

2. The compound as recited in claim 1 wherein $R^1$ is phenyl, 4-methoxyphenyl or 1-naphthyl; $R^2$ is cyclopropylmethyl, 4-imidazolylmethyl, 2-thienylmethyl, 4-thiazolylmethyl, 2-methyl-4-thiazolylmethyl or 2-amino-4-thiazolylmethyl; $R^3$ is 2-methylpropyl, cyclopropylmethyl, cyclohexylmethyl or benzyl, and $R^4$ is lower alkyl or lower cycloalkyl.

3. The compound as recited in claim 1 wherein $R^1$ is phenyl; $R^2$ is cyclopropylmethyl, 4-thiazolylmethyl or 2-amino-4-thiazolylmethyl; $R^3$ is cyclohexylmethyl; and $R^4$ is 2-methylpropyl or cyclopropyl.

4. The compound as recited in claim 1 selected from the group consisting of:
- (2R, 4S, 5S)-N-[1(S)-(cyclohexylmethyl)-2(R),3(S)-dihydroxy-5-methylhexyl]-2-(cyclopropylmethyl)-4,5-dihydroxy-6-phenylhexanamide,
- (2R, 4R, 5R)-N-[1(S)-(cyclohexylmethyl)-2(R), 3(S)-dihydroxy-5-methylhexyl]-2-(cyclopropylmethyl)-4,5-dihydroxy-6-phenylhexanamide,
- (2R, 4S, 5R)-N-[1(S)-(cyclohexylmethyl)-2(R), 3(S)-dihydroxy-5-methylhexyl]-2-(cyclopropylmethyl)-4,5-dihydroxy-6-phenylhexanamide,
- (2R, 4R, 5S)-N-[1(S)-(cyclohexylmethyl)-2(R), 3(S)-dihydroxy-5-methylhexyl]-2-(cyclopropylmethyl)-4,5-dihydroxy-6-phenylhexanamide,
- (2R, 3S, 5R)-N-[1(S)-cyclohexylmethyl)-2(R), 3(S)-dihydroxy-5-methylhexyl]-2-(cyclopropylmethyl)-3,5-dihydroxy-6-phenylhexanamide,
- (2R, 3R, 5R)-N-[1(S)-cyclohexylmethyl)-2(R), 3(S)-dihydroxy-5-methylhexyl]-2-(cyclopropylmethyl)-3,5-dihydroxy-6-phenylhexanamide,
- (2R, 3 R, 5S)-N-[1 (S)-(cyclohexylmethyl)-2(R), 3(S)-dihydroxy-5-methylhexyl]-2-(cyclopropylmethyl)-3,5-dihydroxy-6-phenylhexanamide,
- (2R, 3S, 5S)-N-[1(S)-(cyclohexylmethyl)-2(R), 3(S)-dihydroxy-5-methylhexyl]-2-(cyclopropylmethyl)-3,5-dihydroxy-6-phenylhexanamide,
- (2R, 4R, 5R)-N-[1(S)-(cyclohexylmethyl)-2(R), 3(S)-dihydroxy-5-methylhexyl]-4,5-dihydroxy-2-(4-imidazolylmethyl)-6-phenylhexanamide,
- (2S, 4S, 5S)-N-(1(S)-(cyclohexylmethyl)-2(R), 3(S)-dihydroxy-5-methylhexyl]-4,5-dihydroxy-2-(2-thienylmethyl)-6-phenylhexanamide, and
- (2R, 4S, 5S)-2-(2-methyl)-4-thiazolymethyl)-N-[1(S)-(cyclohexylmethyl)-2-(R), 3(S)-dihydroxy-5 -methylhexyl]-4,5-dihydroxy-6-phenylhexanamide.

5. A pharmaceutical composition of matter comprising a compound of formula 1 as recited in claim 1 and a pharmaceutically acceptable carrier.

6. A method for treating renin-dependent hypertension in a mammal comprising administering to said mammal a therapeutically effective amount of a compound of formula 1 as recited in claim 1.

7. A method for treating congestive heart failure in a mammal comprising administering to said mammal a therapeutically effective mount of a compound of formula 1 as recited in claim 1.

* * * * *